United States Patent [19]
Nelson

[11] 4,262,666
[45] Apr. 21, 1981

[54] INHALATOR-BREATHING APPARATUS

[76] Inventor: Byron G. Nelson, P.O. Box 6457, Lake Charles, La. 70606

[21] Appl. No.: 88,043

[22] Filed: Oct. 24, 1979

[51] Int. Cl.³ .......................................... A61M 15/06
[52] U.S. Cl. ......................... 128/203.23; 128/204.13; 128/136
[58] Field of Search ...................... 128/203.12, 202.28, 128/203.23, 203.24, 204.13, 207.14, 136, 205.27, 202.21, 200.24, 203.15; 131/190, 191; 433/91, 93, 140

[56] References Cited

U.S. PATENT DOCUMENTS

| | | | |
|---|---|---|---|
| 836,523 | 11/1906 | Moore | 128/203.12 X |
| 3,998,226 | 12/1976 | Harris | 128/203.15 X |
| 4,192,309 | 3/1980 | Poulsen | 128/203.15 |

Primary Examiner—Henry J. Recla

[57] ABSTRACT

A singularly compact inhalator-breathing apparatus is disclosed which fits inside the mouth of a human between the teeth and cheek and functions to controllably mix ambient air with other gases or gas-like material suspensions during the physiological process of inhaling and conveys the inhalant mixture to the rear of the mouth and on to the lungs. The apparatus is capable of transmitting either into or out of the mouth and lungs a flow of air approximate that flow of air which could be expected through normal nasal breathing.

23 Claims, 9 Drawing Figures

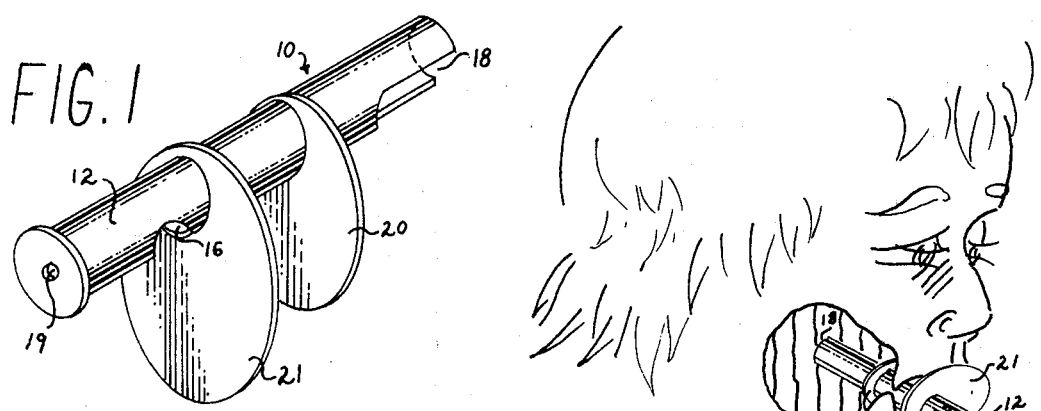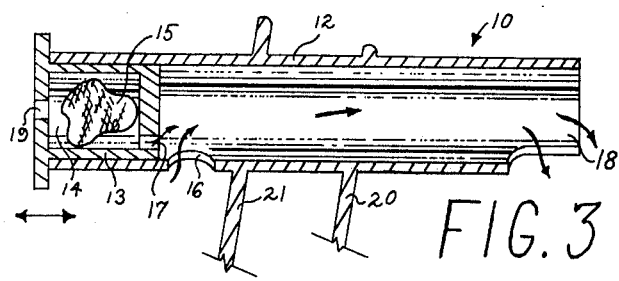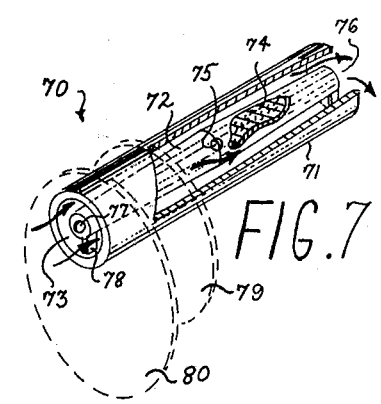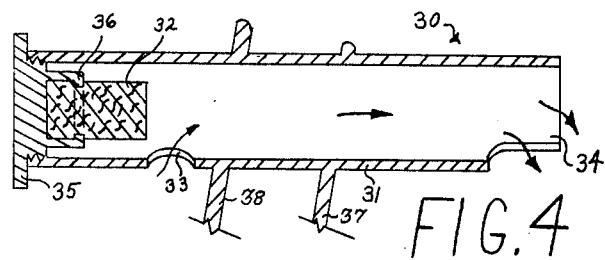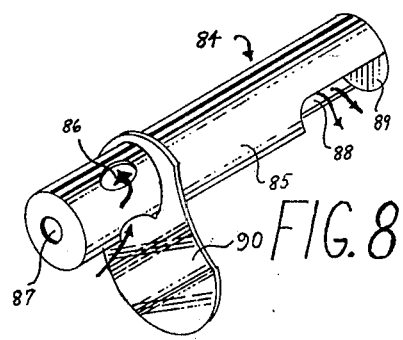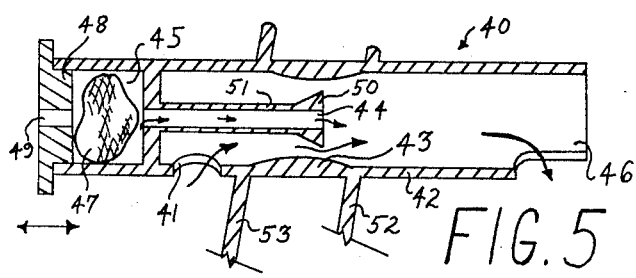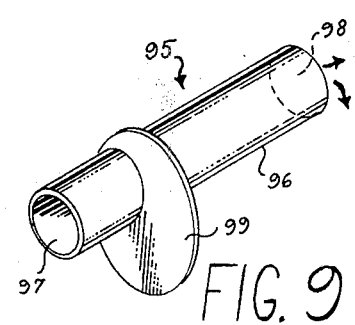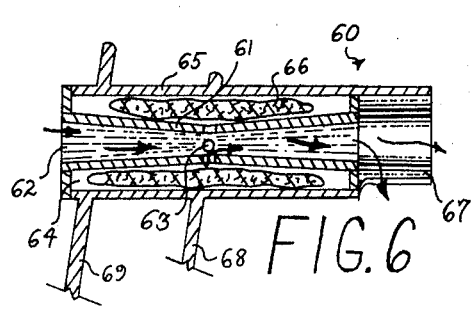

INHALATOR-BREATHING APPARATUS

Application Ser. Nos. 97,325 and 89,035 and 99,855 are related cross references.

BACKGROUND OF THE INVENTION

There are many people who are bothered with a nasal blockage which hinders their breathing, especially at night when they are attempting to sleep. Means are sought by people so afflicted to either promote comfortable mouth breathing by simply avoiding the nasal function with such apparatus as disclosed in Nelson U.S. Pat. No. 4,170,230 or by treating the symptoms of the nasal congestion with nasal sprays, tube inhalators, other various ethical or proprietary drugs in the form of pills, capsules, or liquids, and with mechanical atomizers or steam vaporizers. Except for the mechanical atomizers and steam vaporizers, the above-mentioned methods of treating the symptoms of nasal congestion are not entirely satisfactory because these treatments must be intermittently administered in timed dosages with such periodic administration of these medications evidencing the great defect of requiring both a special mental effort and a repetitive physical act on the part of the user of these medicines and methods. Furthermore, experience has shown that the chemically active ingredients of such periodic dosage medications are necessarily strong acting upon first administration and may result in such irritating side effects upon the user as stomachache, sore nasal and throat membranes, and even altered metabolism. Steam vaporizers and mechanical atomizers demand less recurrent physical action or mental effort on the part of the user and deliver the more desirable continuously uniform dosages of mild yet effective medications, but, such devices are not entirely satisfactory since they exhibit the failings of being cumbersome to use, being lacking in portability, and requiring external electrical or gas means to activate them; furthermore, much of the inhalant material is lost and wasted to the surrounding atmosphere thus rendering many of the devices highly inefficient and unacceptable for prescribed dosages of inhalant.

It is therefore an object of this invention to provide an inhalator-breathing apparatus which the user can place inside the mouth that will function to mix ambient air with other gases or gas-like material suspensions during the physiological process of inhaling and to direct this inhalant mixture through the mouth to the lungs without subjecting the mouth to the drying or deleterious effects of an inhalant mixture.

It is another object of this invention while accomplishing the above object, to transmit into the air stream a measureable amount of gas or gas-like material suspension thereby providing for predictable dosages of the inhalant.

It is another object of this invention, while accomplishing the above objects, to convey as required the approximate flow of air into or out of the mouth as would be expected during normal nasal respiration.

It is another object of this invention, while accomplishing the above objects, to minimize the flow of expiring air into or through the contained source of gas or gas-like material suspension, thereby preserving the efficiency of this inhalant source and minimizing the loss of the gas-like material suspension during the process of exhaling.

It is still another object of this invention to accomplish the above objects without requiring special mental effort or repetitive physical action on the part of the user other than such as is irreducibly needed to satisfy immediate respiratory needs.

It is yet another object of this invention to accomplish the above objects with an apparatus which is singularly compact and portable.

THE INVENTION

This invention relates to a compact inhalator-breathing apparatus which fits inside the mouth of a human between teeth and cheek and which apparatus includes: a tube having a constricted interior region; an air intake opening in said tube; a container element integral with said tube, said container element adapted to hold a source of gas or gas-like material suspension; at least one orifice communicating said integral container element with the interior of said tube, the location of said orifice cooperating with said constricted region of said tube to controllably mix accelerated inhaled air with gas or gas-like material suspension emanating from said integral container through said orifice in the manner of the venturi principle; and at least one exhaust opening adapted to pass the inhalant-air mixture from the tube into the rear of the mouth and on to the lungs. The exhaust opening may be adapted to face at least in part the interior of the mouth. The intake opening with said exhaust opening is sized in combination with the cross-sectional area of said constricted region to provide a flow of air through said tube approximate the flow of air that a human could achieve through normal nasal breathing.

As can be seen from the above, the apparatus of this invention, when placed inside the mouth and subjected to the physiological function of inhaling, will mix large quantities of ambient air with continuously controlled small quantities of gas-like material suspension and convey this mixture to the rear of the mouth and into the lungs, thus making it possible for the user to derive from such an inhalant mixture an uninterrupted physiological satisfaction without the requirement of special mental effort or repetitive physical action. By routing the air-inhalant mixture to the rear of the mouth the user of this invention avoids exposing his or her mouth to the drying and deleterious effects of an otherwise uncontained air-inhalant passage over and through the several parts of the mouth. There is additionally provided a sealing element attached to the apparatus; said sealing element extends across the front of the mouth to an extent of effecting a seal in the event the mouth is opened during sleep; the air-inhalent is thereby prevented from passing through the mouth except through the tube portion of the inhalator-breathing apparatus.

These and other features of the invention contributing satisfaction in use and economy in manufacture will be more fully understood when taken in connection with the following description and illustrations in which identical numerals refer to identical parts and in which:

FIG. 1 is a perspective view of one embodiment of this invention;

FIG. 2 is a view of the apparatus shown in FIG. 1 in place in a human mouth;

FIG. 3 is a sectional view of the embodiment of the invention shown in FIG. 1;

FIG. 4 is a sectional view of a second embodiment of this invention;

FIG. 5 is a sectional view of a third embodiment of this invention;

FIG. 6 is a sectional view of a fourth embodiment of this invention;

FIG. 7 is a perspective view of a fifth embodiment of this invention with a cut away section showing the inner container element configuration and the air flow path;

FIG. 8 is a perspective view of a sixth embodiment of the invention showing the singular stabilizing means; and FIG. 9 is a perspective view of a seventh embodiment of the invention showing the singular sealing means.

Referring now to the embodiments shown in FIGS. 1, 2, and 3 it can be seen that the breathing apparatus of this invention generally designated by the numeral 10 includes an air flow tube 12 and a container element 13 integral thereto having a cavity 14, therein a source of gas-like material suspension 15. When respirated air enters upstream opening 16, the air is accelerated thereby causing a reduction in air pressure in the vicinity of orifice 17. Orifice 17 communicates with cavity 14 of container element 13. Gaseous material suspension emanating from source 15 exits cavity 14 by way of orifice 17 and combines with the inflowing air to move in the direction of the arrows to exit tube 12 through downstream rear opening 18. Pressure balance port 19 communicates the atmosphere with cavity 14 and allows external air to enter the container element cavity 14 during the inhalation process, however, it is to be understood that in some cases when greater gas flow control is desired, container element 13 may be made without pressure balance port 19, since upon exhalation there will be a reversal of air flow through orifice 17 into cavity 14 thereby reestablishing the pressure potential of said cavity 14. The drawings show sealing means 20 which is adapted to fit between the frontal teeth and lips thereby effecting an air seal so that air flows only into or out of tube 12. Sealing means 20 may be flexible or rigid; when sealing means 20 is of a rigid nature it should be made curved to conform to the outer curvature of the frontal mouth for best results. Stabilizing flange means 21 prevents swallowing the apparatus thereby promoting comfort and safety to the user in wearing the apparatus. Stabilizing means 21 may also serve to limit the depth into the user's mouth the tube 12 of this invention projects, since stabilizing means 21 should contact the outer lip area when the apparatus is placed in the mouth. The drawing shows apparatus of this invention 10 having one upstream air opening 16 and one orifice 17, however, there may be a plurality of upstream air openings 16 as when, for instance, said openings are radially oriented about the tube, and there may be a plurality of orifices 17. When there is a plurality of upstream air openings 16, there should be at least one orifice 17 in container element 13 located proximate each upstream air opening 16 for best gas-flow properties. The source of gas-like material suspension 15 may be constructed of cloth-like material or fibrous material, with said materials saturated with aromatic substances or medicinal powders in the manner well known to those familiar with the inhalator art, or the source 15 may even be a more solid material which evaporates at least in part into gas-like material suspension.

It can be seen in FIG. 3 that container element 13 is removable from tube 12, thereby allowing for replenishing of the apparatus of this invention with another like element 13 as gas source 15 is used up.

FIG. 4 shows the apparatus of this invention generally designated by the numeral 30, and includes an air flow tube 31, and a source of gas-like material suspension 32. The source of gas-like material suspension 32 is exposed to the inhaled air which passes through upstream opening 33 and directly contacts gas-like material suspension emanating from the source 32 wherefrom a mixture of the gas and air moves through tube 31 to exit downstream rear opening 34. Gas source 32 is held in place within the tube by holding element 35 which has retentive node 36 embedded in gas source 32. Gas source 32 with holding element 35 is removable from tube 31 so that source 32 may be replaced as needed. Alternative means for maintaining gas source 32 in place on holding element 35, instead of retentive node 36, could be web-like mesh, with said mesh surrounding source 32 and being attached to holding element 35. The drawing shows sealing means 37 and stabilizer 38, all the attributes of which can be found in the discussion of FIGS. 1, 2, and 3 above about sealing means 20 and stabilizer 21.

FIG. 5 shows another embodiment of the breathing apparatus generally designated by the numeral 40. Air enters upstream inlet port 41 and moves along the interior of tube 42 to an area of flow restriction defined by a venturi shaped configuration 43 of the tube 42 wall. Air flow accelerates through venturi shaped configuration 43 thereby causing a reduction in pressure in the vicinity of orifice 44. Gaseous material from cavity 45 emanates from orifice 44 and combines with the accelerated air in the manner of the venturi principle and the air-gas mixture exits tube 42 through downstream opening 46. The source 47 of gaseous material is retained within cavity 45 by removeable retainer means 48. The drawing shows orifice 49 in retainer 48 through which regenerative air may flow into cavity 45; however, such an orifice 49 may not be necessary as exhaled air in tube 42 will regenerate pressure potential in cavity 45 through orifice 44. Flared end 50 of orifice capillary tube 51 serves the purpose of further restricting inhaled air flow through tube 42, thereby bringing about accelerated air flow when inhaling with a resultant drop in pressure in the vicinity of the orifice 44. It is to be understood that any of the well known means for restricting air flow thereby accelerating air flow in tube 42 during inhalation may serve the purpose of this invention; for instance an orifice plate or flow nozzle fashioned in the tube 42 wall would be satisfactory. Likewise, simply flaring the orifice 44 end of capillary tube 51 without utilizing any of the other above mentioned means of accelerating air flow would also suffice. Sealing means 52 and stabilizer 53 function as per the discussion for sealing means 20 and stabilizer 21 above.

Referring now to FIG. 6, it can be seen in the embodiment generally designated by the numeral 60 how inhaled air enters tube 61 through front opening 62. Tube 61 has a venturi shaped interior configuration with orifices 63 located radially in the wall of tube 61, and proximate the constricted region of the tube 61. There may be instances when one orifice 63 will suffice. Orifices 63 communicate the interior of tube 61 with cavity portion 64 of containing element 65 which coaxially surrounds tube 61. Contained in the cavity portion 64 is source of gaseous matter 66. The resultant drop in pressure in the vicinity of orifices 63 as the air accelerates causes gaseous matter to exit cavity 64 through orifices 63 and enter the air stream within axially disposed tube 61. The mixture of air and gases exits tube 61 through downstream rear opening 67. Sealing means 68 and stabilizer 69 adhere to the discussion of seal 20 and stabilizer 21 above.

FIG. 7 shows another embodiment generally designated by the numeral 70, wherein air flow tube 71 has axially disposed within it container element 72. Inhaled air enters front upstream opening 73 of tube 71 and is accelerated by means of a restriction in the air flow path defined by the bulbous external configuration of container element 72. Contained within container element 72 is gaseous matter source 74. Located proximate the air flow restriction and communicating the interior of container element 72 with the interior of flow tube 71 is orifice 75, thereby allowing gaseous matter to exit the interior of container element 72, and enter the accelerated air stream with the resultant mixture exiting tube 71 through rear opening 76. Pressure equalizing port 77 communi- the atmosphere with the interior of container element 72, and may not be necessary in some instances where more strident control of gas flow from orifice 75 is indicated. Container element 72 is held in position by holding means 78. Shown in phantom lines are sealing element 79 and external flange stablizer means 80; the attributes of each are to be found in the discussion of sealing means 20 and stabilizer 21 in FIGS. 1, 2, and 3 above.

FIG. 8 shows an embodiment of this invention generally designated by the numeral 84, wherein air flow tube 85 has radially oriented air openings 86. Air balance port 87 is shown in the end of the tube 85 with said balance port communicating the atmosphere with a gas-source therein. Also shown proximate the closed end 89 of tube 85 is downstream air opening 88 adapted to face the inside of the mouth. External stabilizer means 90 is shown attached to the upstream portion of flow tube 85 and is of a shape to fit comfortably in contact with the exterior of the lips when apparatus 84 is in the mouth.

FIG. 9 shows a last embodiment of the invention generally designated by the numeral 95 consisting of flow tube 96 with front opening 97 and back opening 98, and sealing means 99 adapted to fit between the frontal teeth and lips of the user of the invention.

There may ocurr instances when the user of the apparatus is a patient of extensive mouth surgery whereby the device is removed and replaced often in the mouth; FIG. 9 shows generally a device having no sealing means per se, but only external stablizing means for use on such occasions. Likewise, it can be seen in FIG. 8 how the apparatus of the invention may be generally constructed without external stabilizer means while still retaining the sealing means for use in some instances of lip injury when an external stabilizer may aggravate the wound. It is to be understood, therefore, that the embodiments shown in FIGS. 1 through 7 may, though with some loss of design efficiency, be constructed in accordance with the generally described embodiments shown in FIGS. 8 and 9 to satisfy either of the two above mentioned needs.

The strength of the air to gas mixture can be predictably controlled by various methods such as: fixing the orifice size in accordance with a known strength of the gas source, compounding the gas source strength in accordance with a known orifice size, varying the orifice location relative to the constricted region in the air flow path while still maintaining the venturi effect, and by constructing the integral container with or without an opening to the atmosphere thereby regulating the amount of pressure in the container relative to the venturi action applied to the orifice, or even constructing the container element with a flexible diaphragm having one side exposed to ambient air pressure and the other side facing the cavity.

The apparatus of this invention may be constructed of any materials known to the medical or dental art, such as latex rubber or plastics which are inert in the human mouth. The invention may be manufactured by means of molding, extrusion, injection molding, casting, etc.

What is claimed is:

1. An inhalator-breathing apparatus fitable inside the mouth of a human between cheek and teeth which apparatus comprises: elongated tube means having at least one upstream opening adapted to communicate the interior of said tube means with the atmosphere and at least one downstream opening adapted to communicate said interior of said tube means with the rear portion of said mouth, said tube means being adapted and of a length sufficient to extend from the front of the mouth back down the side of the mouth to a point adjacent the molars; retainer means disposed integrally within said tube means, a prepared source of gas-like material suspension retained in said tube means by said retainer means so that inhaled air flowing through said tube means will contact at least in part a gas-like material suspension emanating from said prepared source of gas-like material suspension therby generating an air to gas mixture transferable to said rear portion of said mouth by way of said downstream opening; and sealing means adapted to fit at least in part between frontal teeth and lips being attached to the upstream portion of said tube means thereby to seal off the flow of air through said mouth except into said tube means through said upstream opening; said upstream opening and said downstream opening in combination with the cross sectional area of said interior of said tube means being of a size sufficient to allow a flow of air through said tube means approximate to the flow of air said human could achieve through normal nasal breathing.

2. The apparatus of claim 1 wherein said prepared source of gas-like material suspension is fibrous material treated with an aromatic substance.

3. The apparatus of claim 1 wherein said downstream opening is adapted to face at least in part the interior of said mouth.

4. The apparatus of claim 1 wherein there is additionally provided flange stabilizing means attached to said tube means, said flange stabilizing means adapted for fitment externally of the lips.

5. The apparatus of claim 1 wherein said source of gas-like material suspension is removeable from said tube means.

6. An inhalator-breathing apparatus fitable inside the mouth of a human between cheek and teeth which apparatus comprises: integral retainer member having a cavity for containing; therein a prepared source of gas-like material suspension; elongated tube means having at least one upstream opening adapted to communicate the interior of said tube means with the atmosphere, and at least one downstream opening adapted to communicate said interior of said tube means with the rear portion of said mouth; said tube means being adapted and of a length sufficient to extend from the front of said mouth down the side of said mouth to a point adjacent the molars; at least one orifice communicating the interior of said tube means with said cavity of said retainer member so that gas-like material suspension contained therein will have access to said interior of said tube means for mixing with inhaled air flowing therethrough, with said mixture exiting said tube means through said downstream opening into the mouth; sealing means adapted to fit at least in part between the frontal teeth and lips being attached to the upstream portion of said tube means thereby to seal off the flow of air through said mouth except into said tube means through said upstream opening; said upstream opening and said downstream opening being in combination with the cross-sectional area of said interior of said tube means a size sufficient to allow a flow of air through said tube means approximate to the flow of air said human could achieve through normal nasal breathing.

7. The apparatus of claim 6 wherein said containing member additionally includes an orifice communicating said cavity of said retainer member with the atmosphere.

8. The apparatus of claim 6 wherein said prepared source of gas-like material suspension is fibrous material treated with an aromatic substance.

9. The apparatus of claim 6 wherein said tube means has a restriction in the air flow path by means of said restriction the inhaled air is accelerated and reduced in pressure; there being located proximate said restriction at least one said orifice communicating said interior of said tube means with said cavity in said retainer member thereby permitting a flow of gas-like material suspension from said cavity into the area of reduced pressure within the interior of said tube means.

10. The provision in claim 9 wherein said restriction is a venturi tube shaped configuration.

11. The apparatus of claim 6 wherein said downstream opening is adapted to face at least in part the interior of said mouth.

12. The apparatus of claim 6 wherein there is additionally provided flange stabilizing means attached to said tube means, said flange stabilizing means adapted for fitment externally of the lips.

13. The apparatus of claim 6 wherein there is additionally provided capillary tube means extending from said orifice in said retainer member to a point proximate said interior of said tube means thereby defining a gas-like material suspension flow path from said cavity of said retainer member to said interior of said tube means.

14. An inhalator-breathing apparatus fitable inside the mouth of a human between cheek and teeth which apparatus comprises: elongated tube means having at least one upstream opening adapted to communicate the interior of said tube means with the atmosphere and at least one downstream opening adapted to communicate said interior of said tube means with the rear portion of said mouth; said tube means being adapted and of a length sufficient to extend from the front of said mouth back down the side of said mouth to a point adjacent the molars; retainer means disposed integrally within said tube means, a prepared source of gas-like material suspension retained in said tube means by said retainer means so that inhaled air flowing through said tube means will contact at least in part a gas-like material suspension emanating from said prepared source of gas-like material suspension thereby generating an air to gas mixture transferable to said rear portion of said mouth by way of said downstream opening; said upstream opening and said downstream opening in combination with the cross-sectional area of said interior of said tube means being of a size sufficient to allow a flow of air through said tube means approximate to the flow of air said human could achieve through normal nasal breathing; stabilizing means affixed to said tube means, said stabilizing means being adapted for fitment externally of the lips.

15. The apparatus of claim 14 wherein said prepared source of gas-like material suspension is fibrous material treated with an aromatic substance.

16. The apparatus of claim 14 wherein said downstream opening is adapted to face at least in part the interior of said mouth.

17. The apparatus of claim 14 wherein said source of gas-like material suspension is removeable from said tube means.

18. An inhalator-breathing apparatus fitable inside the mouth of a human between cheek and teeth which apparatus comprises: integral containing member having a cavity for containing; therein a prepared source of gas-like material suspension; elongated tube means having at least one upstream opening adapted to communicate the interior of said tube means with the atmosphere, and at least one downstream opening adapted to communicate said interior of said tube means with the rear portion of said mouth; said tube means being adapted and of a length sufficient to extend from the front of said mouth down the side of said mouth to a point adjacent the molars; at least one orifice communicating the interior of said tube means with said cavity of said containing member so that gas-like material suspension contained therein will have access to said interior of said tube means for mixing with inhaled air flowing therethrough, with said mixture exiting said tube means through said downstream opening into the mouth; said upstream opening and said downstream opening being in combination with the cross-sectional area of said interior of said tube means a size sufficient to allow a flow of air through said tube means approximate to the flow of air said human could achieve through normal nasal breathing; stabilizing means affixed to said tube means, said stabilizing means being adapted for fitment externally of the lips.

19. The apparatus of claim 18 wherein said containing member additionally includes an orifice communicating said cavity of said containing member with the atmosphere.

20. The apparatus of claim 18 wherein said tube means has a restriction in the air flow path by means of said restriction the inhaled air is accelerated and reduced in pressure; there being located proximate said restriction at least one said orifice communicating said interior of said tube means with said cavity of said containing member thereby permitting a flow of gas-like material suspension from said cavity into the area of reduced pressure within the interior of said tube means.

21. The provision in claim 20 wherein said restriction is of a venturi tube shaped configuration.

22. The apparatus of claim 18 wherein said downstream opening is adapted to face at least in part the interior of said mouth.

23. The apparatus of claim 18 wherein there is additionally provided capillary tube means extending from said orifice in said containing member to a point proximate said interior of said tube means thereby defining a gas-like material suspension flow path from said cavity of said containing member to said interior of said tube means.

* * * * *